(12) United States Patent
Schultz et al.

(10) Patent No.: US 10,729,588 B2
(45) Date of Patent: Aug. 4, 2020

(54) FINGERSTALL

(71) Applicant: TECHNISCHE UNIVERSITÄT DRESDEN, Dresden (DE)

(72) Inventors: Jurek Schultz, Dresden (DE); Guido Fitze, Dresden (DE)

(73) Assignee: TECHNICHE UNIVERSITÄT DRESDEN, Dresden (DE)

( * ) Notice: Subject to any disclaimer, the term of this patent is extended or adjusted under 35 U.S.C. 154(b) by 458 days.

(21) Appl. No.: 14/774,997

(22) PCT Filed: Mar. 13, 2014

(86) PCT No.: PCT/DE2014/100088
§ 371 (c)(1),
(2) Date: Sep. 11, 2015

(87) PCT Pub. No.: WO2014/139518
PCT Pub. Date: Sep. 18, 2014

(65) Prior Publication Data
US 2016/0022501 A1    Jan. 28, 2016

(30) Foreign Application Priority Data
Mar. 14, 2013    (DE) .................. 10 2013 102 609

(51) Int. Cl.
*A61F 13/00* (2006.01)
*A61F 13/10* (2006.01)

(52) U.S. Cl.
CPC .. *A61F 13/00068* (2013.01); *A61F 13/00017* (2013.01); *A61F 13/00038* (2013.01);
(Continued)

(58) Field of Classification Search
CPC .................................................... A61F 13/105
(Continued)

(56) References Cited

U.S. PATENT DOCUMENTS

| 835,803 A | * | 11/1906 | Witten | A61F 13/105 |
| | | | | 602/58 |
| 2,571,946 A | * | 10/1951 | Rosenfield | A61F 13/105 |
| | | | | 602/1 |

(Continued)

FOREIGN PATENT DOCUMENTS

| DE | 375555 C | 5/1923 |
| FR | 2715832 A1 | 8/1995 |

(Continued)

OTHER PUBLICATIONS

International Preliminary Report on Patentability dated Sep. 15, 2015, including the Written Opinion of the Search Authority and English translation thereof, in connection with corresponding Application No. PCT/DE2014/100088 (12 pgs.).

(Continued)

*Primary Examiner* — Anna K Kinsaul
*Assistant Examiner* — Caitlin A Carreiro
(74) *Attorney, Agent, or Firm* — Maier & Maier, PLLC

(57) ABSTRACT

A fingerstall, in particular for treatment of defects of the distal phalanx of the finger with a closed distal end, an open proximal end, and an interior. Provision is made that a chamber is formed in the fingerstall at the distal end thereof and the chamber is in liquid communication with the interior of the fingerstall.

13 Claims, 5 Drawing Sheets

(52) U.S. Cl.
CPC .. *A61F 13/105* (2013.01); *A61F 2013/00093* (2013.01); *A61F 2013/00119* (2013.01); *A61F 2013/00272* (2013.01)

(58) Field of Classification Search
USPC ..... 2/21; 602/23, 63, 22, 54, 5, 21; 128/880
See application file for complete search history.

(56) References Cited

U.S. PATENT DOCUMENTS

| | | | | |
|---|---|---|---|---|
| 4,507,807 | A | * | 4/1985 | Karkanen .......... A41D 19/0055 2/161.8 |
| 4,813,406 | A | * | 3/1989 | Ogle, II .............. A61F 5/05875 602/22 |
| 4,942,626 | A | * | 7/1990 | Stern ...................... A61B 42/10 2/161.7 |
| 5,819,765 | A | * | 10/1998 | Mittiga ................... A46B 5/04 132/309 |
| 7,789,845 | B1 | * | 9/2010 | Meliti .................. A41D 13/087 2/163 |
| 2010/0234785 | A1 | * | 9/2010 | Liebowitz ............. A61F 5/0118 602/61 |
| 2012/0210486 | A1 | * | 8/2012 | McJunkin ............ A41D 13/087 2/69 |

FOREIGN PATENT DOCUMENTS

| | | |
|---|---|---|
| GB | 19869 A | 8/1914 |
| GB | 446944 A | 5/1936 |
| GB | 540241 | 8/1940 |
| GB | 540241 A | 10/1941 |

OTHER PUBLICATIONS

M. Richter, "Fingerkuppendefekte", in Obere Extremität, vol. 5, 2010, pp. 6-13 (8 pgs.).
P. de Boer, "The Use of Silver Sulphadiazine Occlusive Dressings for Finger-Tip Injuries", in Journal of Bone and Joint Surgery (JBJS) (Br), vol. 63-B, No. 4, 1981, pp. 545-547 (3 pgs.).
International Search Report dated Jun. 13, 2014 from corresponding International Patent Application No. PCT/DE2014/100088; 6 pgs.

* cited by examiner

FINGERSTALL

FIELD

The invention relates to a fingerstall that in particular can be used for treatment of defects of the distal phalanx of the finger. Moreover, it relates to a kit comprising such fingerstalls.

BACKGROUND

The distal phalanx of the finger forms the distal end of a finger. It comprises the finger pad also referred to as fingertip. The fingertip is bounded to the outside by the skin that is attached to the distal phalanx bone via connective tissue. The fingertips as part of the prehensile apparatus are loaded upon grasping. In humans, the fingertips particularly participate in the pinch grip, writing grasp and lateral pinch. The skin of human fingertips has a number of different receptors, e.g. mechanoreceptors, nociceptors, and thermoreceptors. These receptors provide for the high sensitivity of the fingertips so that the fingertips in addition to the prehensile function also possess a sensory function.

The treatment of injuries of the fingertip is to restore both its prehensile function and its sensory function as far as possible. Here, the length of the fingertip, its sensitivity, resistance, and aesthetic appearance should be maintained or restored as well as hypersensitivity avoided. While minor injuries, i.e. injuries of the skin and the connective tissue in the millimeter range, can be repaired by secondary wound healing, i.e. with cicatrization, major injuries, i.e. injuries in which the finger bone participates, beyond this may require more complex treating processes of the plastic surgery. Among these, there are in particular the coverage with skin transplants, local lobuli or neurovascularly stalked flap plastics. For detail, see Richter, M., Fingerkuppendefekte, Obere Extremität (5) 2010, 6-13.

However, operative cares are cost-intensive treatments by highly specialized staff, and associated with an anesthesia, cicatrization and regular change of dressing. Restitutio ad integrum is not possible.

However, it has turned out that the treatment of defects of the distal phalanx of the finger with semi-occlusive dressings can be of advantage even with major injuries. Such a semi-occlusive dressing can be prepared by means of gauze. In both cases, the defect surface can be treated with silver sulphadiazine. Furthermore, semi-occlusive dressings are known in which a specific film is employed that should allow the formation of a specific wound environment at the wound. It is assumed that said wound environment comprising a number of growth factors that promote the synthesis of collagen allows a rapid re-epithelialization. In practice, these dressings are often referred to as occlusive dressings although in fact, these dressings are not occlusive, i.e. dense dressings. All of the known films, ointment-gauzes, rubber gloves etc. that are used to prepare these dressings according to the prior art are associated with leakages so that they are not occlusive, but semi-occlusive dressings. The formation of leakages is due to several factors, in particular to the fact that fingers sweat, capillary forces do act and at least in the first 7 to 14 days after application of the dressing always new wound fluid is formed.

Semi-occlusive dressings are particularly indicated in the treatment of types 1 to 4 defects of the distal phalanx of the finger according to the Allen classification that however only refers to transversal injuries. In case of type 1 defects there is no bone participation and the nail bed is only affected to a limited extent. In case of type 2 defects there is bone participation, moreover the nail bed with respect to its length is preserved to at least 50%. Also with not quite transversal, that is slightly oblique palmar injuries otherwise being like type 2, semi-occlusive dressings can be applied. With extended, strongly oblique palmar injuries up to now the methods of plastic surgery are advised.

The films used for the semi-occlusive dressings by sealing the defect are attached to its edges. Here, a cavity is to be formed between the defect surface and the film wherein the cavity should correspond to "the defect". Further, the film is fixed by means of patches proximal of the defect. Finally, a dressing is applied around film and patch. Richter, loc. cit. considers an at least weakly change of the film to be required. In practice, film changes were necessary all two to three weeks or for the first time after four weeks. The duration of the treatment is between four and six weeks. Details for that are taken from Richter, loc. cit.

However, employment of the films for occlusion of wounds is associated with a number of drawbacks. The application of the films is complicated. It is partially made difficult by the finger's blood humidity and is particularly difficult in uncooperative child patients. There cannot be formed a space that is an adaption of the natural form of the fingertip by means of the film. The film does not mechanically protect the wound from impacts etc. Such a protection can only be effected by additional dressings and splintages that unnecessary immobilize the hand. Also, inactivation of the affected finger requires additional splints. A change of the dressing requires a lot of effort because it requires the elimination of the splint, the bandages and adhesive films, subsequently cleaning and drying of the finger to completely re-apply the dressing. Also, an atraumatic storage of ichor without direct contact with the wound surface is not possible. Moreover, it is not possible to apply healing-promoting agents to the wound without removing the occlusion and thus, disturbing regeneration. Finally, there often occur excessive leakages of the wet space under the conventional film dressing.

De Boer et al., JBJS (Br), 63-B (4) 1981, 545-547, describe the use of a fingerstall in the treatment of defects of the distal phalanx of the finger. The fingerstall was cut off from an "ordinary" surgery glove composed of rubber. First, the cleaned wound was spread with the silver sulphadiazine cream, then the fingerstall was pulled over the finger and its proximal end was attached to the finger by means of an adhesive tape. However, the fingerstall is as leaky as the film dressings so that wound fluid came out of the fingerstall what required a separate instruction of the patients and in addition adversely affects the formation of the healing-promoting wound environment. A further drawback is the inexact formation of the cavity between the inside of the fingerstall and the defect surface. Finally, the change of the fingerstall is as complicated as the change of the films. Thus, the fingerstall suggested by de Boer et al. could not prevail over the films in practice.

A nerve protection device for typists and typesetters is known from DE 375 555. The nerve protection device provides for an air cushion between the fingertip and the outer end of the device. GB 540,241 describes a device for applying a substance onto a body tissue. For that, a chamber is formed in a fingerstall. The substance can be pushed out of the chamber with the finger without a connection being required between the interior of the fingerstall and the chamber.

The technical problem of the invention is to eliminate the drawbacks according to the prior art. In particular, there is provided a fingerstall that allows a simple and better treatment of defects of the distal phalanx of the finger.

According to embodiment of the invention there is provided a fingerstall that is particularly suitable for the treatment of defects of the distal phalanx of the finger and has a closed distal 20 end, an open proximal end, and an interior, wherein a chamber is formed in the fingerstall at the distal end thereof, wherein the chamber is in liquid communication with the interior of the fingerstall.

For use, the fingerstall according to the invention with its open proximal end is pulled over the finger having the defect. Here, the distal phalanx of the finger reaches a portion of the interior that abuts on the chamber. So, the defect is enveloped by the sheath of the fingerstall and the partition wall between the interior and the chamber, so that the defect of the distal phalanx of the finger is semi-occlusively enclosed by means of the fingerstall. The fluid forming during the healing process can enter the chamber. Thus, the chamber forms a reservoir for the wound fluid. Wound fluid entering the chamber and collecting there can be taken out of the chamber for example by means of a cannula that is inserted from the outside through the chamber wall. The cavity of the chamber is preferably spherical or elliptical with other shapes being possible. According to the invention there can be provided fingerstalls with differently sized chambers which allows a fingerstall with a chamber of the desired size to be chosen. Here, there can be chosen a fingerstall having a greater chamber the greater the defect of the distal phalanx of the finger is.

The thickness of the material and the shape of the chamber are chosen such that with a conventional cannula there can always simply be taken wound fluid out of the chamber, preferably about 500 µl, for diagnostic and scientific purposes without removing the fingerstall, disturbing tissue regeneration or hurting the patient. The fingerstall still remains largely tight and does not leak even after multiple punctures. Preferably, the internal volume of the chamber is in the range of 0.1 to 2 ml, wherein in a particularly preferred embodiment the chamber has an internal volume of 500 microliters (µl).

The fingerstall according to the invention allows patients with partial amputations of the distal phalanx of the finger to be treated in a simple and rapid as well as atraumatic way. This applies in particular also to uncooperative patients, that is patients who totally oppose the treatment or at least won't or cannot follow parts of the treatment regime. The fingerstall, in an uncomplicated manner allows to create a semi-occlusive, wet space around the wound surface. It promotes tissue regeneration, so that the aim of a restitutio ad integrum, i.e. scar-free healing, despite the substance defect over the prior art can be obtained in a simpler and better way. With the chamber of the fingerstall provided according to the invention it is possible for the first time to investigate tissue regeneration scientifically, for example microbiologically, molecular-biologically, cytologically etc. without disturbing regeneration or impairing the patient in any way. Furthermore, the chamber may allow atraumatic application of agents to promote regeneration of connective tissue and skin. The fingerstall according to the invention allows a simple and rapid removing from the finger and equally a simple and rapid putting back onto the finger.

The fingerstall may have a region extending from the proximal end of the fingerstall to the walls of the chamber. For example, said region may be in the form of stripes or ribs. Preferably, the width of the region is between a fifth and a third, particularly preferred a fourth of the periphery of the fingerstall. Here, the term "width" of the region relates to its extent in the circumferential direction. In the following, the region is also referred to as reinforced region. When slipping on the fingerstall over a finger the reinforced region suitably lies on the dorsum of a finger. However, it can also lie on the palmar side of the finger or another portion of the finger. The location of the reinforced region can be selected such that the reinforced region provides for a splintage, i.e. inactivation of the finger, and moreover mechanical protection of the wound surface.

Preferably, the fingerstall comprises a rubber-elastic material. In one embodiment, the fingerstall consists of a first rubber-elastic material and a second rubber-elastic material with the second rubber-elastic material being more rigid than the first rubberelastic material. The walls of the chamber can be completely or partially formed of the second rubber-elastic material. Among these walls there are suitably not only the exterior walls of the chamber that at the same time are part of the outside of the fingerstall, but also the internal partition wall between chamber and interior of the fingerstall. Preferably, the partition wall toward the interior has the shape of an intact finger pad or fingertip, that is for example is concave or almost concave. Additionally, it may be concave toward the chamber. The finger pad or fingertip-like shape of the partition wall allows regeneration of the distal phalanx of the finger back to the natural shape.

In addition or as an alternative to the walls of the chamber the reinforced region can be formed of the second rubber-elastic material.

The softer first rubber-elastic material provides for high comfort of the fingerstall and allows slipping on the fingerstall over a finger in an unrolling manner similar to a condom.

Preferably, the rubber-elastic material is a silicone-based rubber-elastic material such as silicone gum or silicone elastomers. In the following, silicone-based rubber-elastic materials are also referred to as "silicone". Here, the known silicones can be employed as they are customary for example for surgery gloves. The silicones should be hypoallergenic and even after weeks of wearing the fingerstall should not adhere to the skin or wound surface.

If the fingerstall according to the invention consists of rubber-elastic materials of different rigidity then preferably both rubber-elastic materials are silicone-based rubber-elastic materials, wherein the second silicone-based rubber-elastic material is more rigid than the first rubber-elastic material. Thus, the first silicone-based rubber-elastic material in the following is referred to as "soft silicone", while the second silicone-based rubber-elastic material is referred to as "hard silicone".

The soft silicone should have a very low rigidity and should be very elastic. For example, the soft silicone may be a silicone gel. By the soft silicone the fingerstall independently adheres to the finger. This can be attributed to a vacuum effect. A wet space is created around the defect of the distal phalanx of the finger in the wound area in which tissue regeneration may take place as in the conventional film dressing. The fingerstall is virtually indestructible and also withstands hard field conditions, in particular also mechanical stresses and dirt, as they occur with children playing outdoors.

If the fingerstall only consists of a single rubber-elastic material, so the reinforced region can have a higher material thickness than the adjacent regions of the fingerstall's sheath. If the fingerstall only consists of a single rubber-elastic material, so this material is preferably the material described above as "soft silicone". One example of a suitable rubber-elastic material is a silicone gel.

The rubber-elastic material the fingerstall consists of provides for an optimum fit of the fingerstall which in turn allows a rapid and safe wound care. The reinforced region of the second rubber-elastic material that in comparison to the first rubber-elastic material has a higher rigidity when using the fingerstall preferably lies on the dorsum of the finger. This at the same time results in a splintage of the affected finger whereby it is sufficiently inactivated during the treatment. The selected rubber-elastic material should have sufficient strength with the strength should not be too high so that resistance to deformation is low and the fingerstall cannot ligate. Moreover, the selected rubber-elastic material should have sufficient fracture toughness so that the fingerstall above all upon putting on does not tear.

According to the invention the chamber is at the distal end of the fingerstall. So the outer walls of the chamber at the same time form the distal end of the fingerstall and an adjacent region of the sheath of the fingerstall. If the outer walls of the chamber consist of the second rubber-elastic material, for example of hard silicone, so the distal end of the fingerstall is protected against stresses. Accordingly, in particular also the wound that with the fingerstall slipped on is close to the partition wall, is particularly protected against mechanical stresses. Preferably, the diameter of the fingerstall starting from the proximal end toward the distal end does not increase.

The interior of the fingerstall and the chamber are in liquid communication with each other. In order to establish such a liquid communication one or more facilities for liquid communication, for example one or more capillaries, channels, tubes, permeable membranes, semi-permeable membranes, and combinations thereof may be formed. Due to the liquid communication excessive wound fluid can drain into the chamber. Here, there may be free diffusion to the wound. Suitably, one of the facilities for liquid communication is arranged axially with respect to the longitudinal axis of the fingerstall.

It can be provided that a fluid passage only from the interior of the fingerstall into the chamber, but not from the chamber into the interior of the fingerstall is possible. This can be achieved with a semi-permeable membrane, for example.

The length of the fingerstall may be varied. For example, long fingerstalls may be shortened at their proximal end in order to adapt the fingerstall to the anatomic condition of the finger to be treated. This is particularly suitable with children and adolescents. Finally, fingerstalls of different diameters can be provided.

The fingerstall according to the invention allows a simple and rapid creation of a well-tolerated, protected semi-occlusive chamber for tissue regeneration on the finger without additional splints or adhesive dressings that also under hard field conditions (for example with children playing outdoors) provides reliable protection. Moreover, it provides access to the wound fluid via a chamber allowing collection of specimen. Said chamber may also be used to apply healing-promoting substances.

By means of the fingerstall according to the invention an adequate care also for severe partial amputations of the distal phalanx of the finger is rapidly and atraumatically achieved without anesthesia, without highly specialized staff, and without excessive tension for the patients, in particular also for children. So, a secure protection of the wound against external influences is obtained without unnecessarily thick dressings, splints, or other extensively immobilizing measures. There is established an access to the wound fluid without disturbing the patient or tissue regeneration, so that diagnostic (e.g. identification of bacterial pathogens) or scientific data from the wound fluid can be gained more easily.

In the part of the sheath that envelops the interior a plurality of additional openings can be formed that connect the interior with the outside of the fingerstall. With these additional openings excess wound fluid that cannot be taken up by the chamber at the top of the fingerstall can be drained in a controlled manner. Thus, in the shaft region of the fingerstall this wound fluid can flow out in a controlled manner and can be collected with a compress or the like. In this way, at the proximal end of the fingerstall there is no summation of two irritative factors acting on the skin: friction by the edge of the fingerstall and moisture due to excess wound fluid. This principle of liquid drain away from the edge of the silicone orthesis can also be applied to other occluding ortheses.

The number of additional openings is preferably between two and ten. Preferably, the openings have a diameter of about 0.5 to 2 mm, particularly preferred about 1 mm. The additional openings may also be formed as capillary connections between the interior and the outside of the fingerstall.

In accordance with the invention there is further provided a kit comprising the fingerstalls according to the invention, wherein the fingerstalls have different diameters. Additionally, the fingerstalls may also have different lengths and/or chambers of different size. Preferably, the kit includes fingerstalls with diameters in five to twelve, preferably nine different sizes. With nine different sizes almost all finger sizes and injuries of children and adolescents between 0 and 15 years can be covered.

Moreover, the kit can comprise a measuring instrument for determining finger diameters. This may be a set of measuring rings with which the finger diameter can rapidly and simply be established on the corresponding finger of the opposite hand. On the basis of the thus obtained measuring result the required diameter of the fingerstall can then be determined and a fingerstall can be selected the diameter of which corresponds to the measured finger diameter.

The fingerstall is particularly useful for the treatment of distal finger injuries, in particular partial amputations of the distal phalanx of the finger or other defects of the distal phalanx of the finger. However, it can also be employed for the treatment of other injuries with substance defect, for example for distal toe injuries. An optionally provided partial reinforcement of the wall of the fingerstall can result in a sufficient inactivation of the injured phalanx. An optionally provided reinforcement of the distal end and the wall(s) of the chamber can optimally protect the wound surface against environmental influences.

The invention is explained in detail below with the help of an example not intended to limit the invention with respect to the drawings. Here,

DETAILED DESCRIPTION

Figure 1:
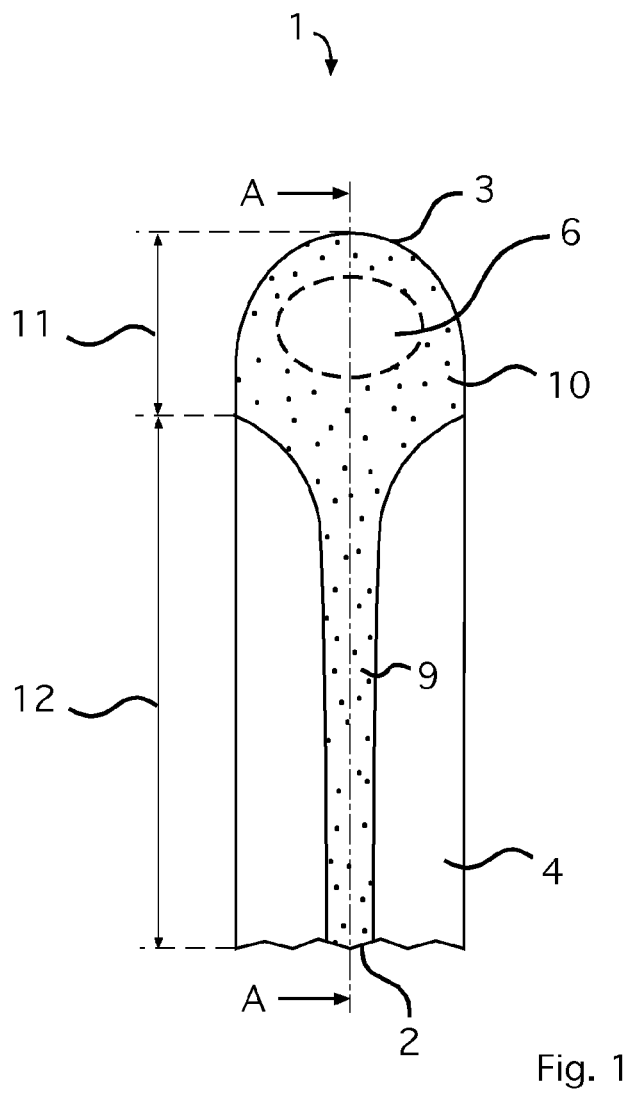
FIG. 1 shows a top view of a first embodiment of a fingerstall according to the invention.
Figure 2:
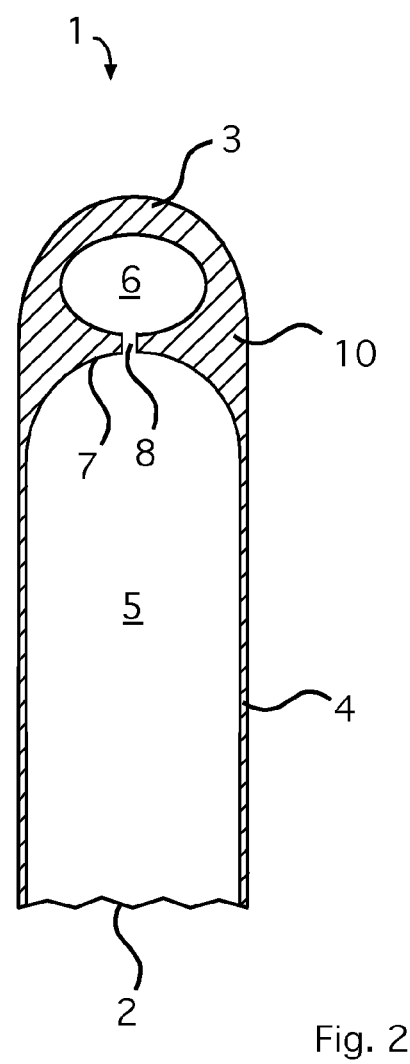
FIG. 2 shows a sectional view of the first embodiment of the fingerstall according to the invention shown in FIG. 1 along the line of cut A-A with the reinforcing element in FIG. 2 not being shown for ease of illustration.

The first embodiment of the fingerstall 1 shown in FIGS. 1 and 2 has a proximal open end 2, a distal closed end 3, and a sheath 4 extending from the proximal end 2 to the distal end 3. The sheath 4 envelops an interior 5 and a chamber 6 that is separated from the interior 5 by a partition wall 7. A capillary 8 is formed in the partition wall 7 that connects the interior 5 with the chamber 6 and allows liquid communication between the interior 5 and the chamber 6. The cavity of the chamber 6 has an elliptical shape. The partition wall 7 toward the interior 5 is formed like a finger pad. The chamber 6 is located at the distal end 3 of the fingerstall 1. The outer wall 10 of the chamber 6 at the same time is part of the outside of the fingerstall 1. When slipping on the fingerstall 1 over a finger the finger reaches the interior 5 of the fingerstall 1.

As can be seen in FIG. 1, the sheath 4 has a strip-like reinforced region 9 extending from the proximal end 2 of the fingerstall 1 up to the chamber 6. When slipping on the fingerstall 1 over a finger the reinforced region 9 should dorsally lie on the finger.

The chamber 6 that is formed by the outer wall 10 and the partition wall 7 forming a cavity as well as the reinforced region 9 of the sheath 4 consist of hard silicone. The remaining parts of the fingerstall, i.e. the sheath 4 except for the reinforced region 9 consist of soft silicone. Both the hard silicone and the soft silicone are rubber-elastic materials. It can be seen in FIGS. 1 and 2 that a portion 11 of hard silicone is formed at the distal end of the fingerstall 1 wherein the chamber 6 is located. On said portion 11 there borders a portion 12 of soft silicone—except for the reinforced element 9—that extends up to the proximal end of the fingerstall 1. In said portion 12 the strip-like reinforced element 9 of hard silicone is formed.

On the outside of the sheath 4 there may be applied an indication of size, for example numbers, that refers to the periphery in the proximal phalanx region of the gypsum dies used for the preparation that were made based on extensive measurements of children's hands.

Figure 3:
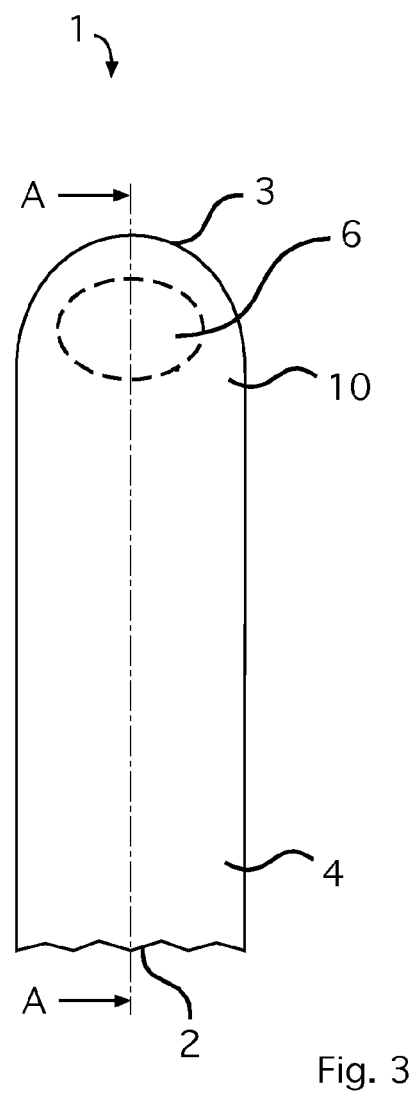
FIG. 3 shows a top view of a second embodiment of a fingerstall according to the invention.

The second embodiment of a fingerstall according to the invention shown in FIG. 3 corresponds to the first embodiment except that the fingerstall 1 only consists of a single rubber-elastic material, namely the soft silicone used in the first embodiment, and no reinforced region is formed.

Figure 4:
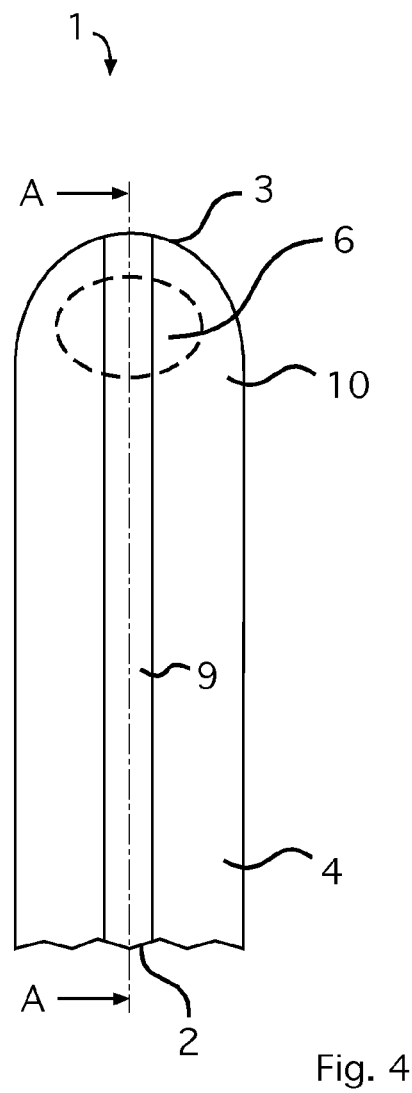
FIG. 4 shows a top view of a third embodiment of a fingerstall according to the invention.

The third embodiment of a fingerstall according to the invention shown in FIG. 4 corresponds to the first embodiment except that the fingerstall 1 only consists of a single rubber-elastic material, namely the soft silicone used in the first embodiment. The reinforced region 9 has a higher material thickness than the regions of the sheath of the fingerstall 1 adjacent to its lengthwise edges.

Figure 5:
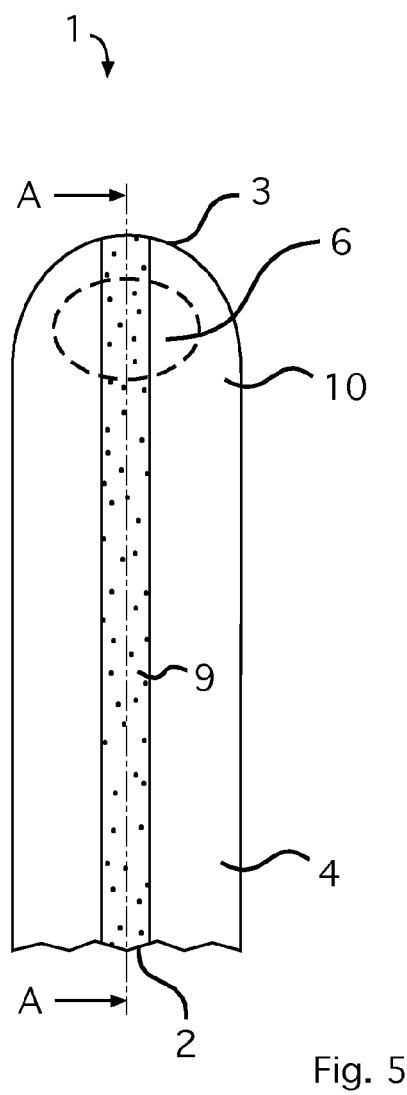
FIG. 5 shows a top view of a fourth embodiment of a fingerstall according to the invention.

The fourth embodiment of a fingerstall according to the invention shown in FIG. 5 corresponds to the first embodiment, except that only the reinforced region 9 of the fingerstall 1 consists of hard silicone, but not the walls of the chamber 6.

The invention claimed is:

1. A fingerstall configured for the treatment of defects of the distal phalanx of the finger, the fingerstall comprising a closed distal end, an open proximal end, and an interior, wherein an enclosed hollow chamber is formed in the fingerstall at the distal end thereof, wherein the enclosed hollow chamber is in liquid communication with the interior of the fingerstall through a fluid channel;

wherein the fingerstall further comprises an outer sheath enveloping an interior portion, said interior portion comprising a cavity defined by an inner surface of the outer sheath, the interior portion separated from the enclosed hollow chamber by a partition wall contiguous with the outer sheath and protruding from the outer sheath in a fixed position, said partition wall configured to prevent ingress of a finger into the enclosed hollow chamber through the fluid channel.

2. The fingerstall according to claim 1, wherein the fingerstall comprises a first rubber-elastic material and a second rubber-elastic material, wherein the second rubber-elastic material is more rigid than the first rubber-elastic material and, wherein walls of the enclosed hollow chamber are formed of the second rubber-elastic material.

3. The fingerstall according to claim 2, wherein the fingerstall additionally has a region that is formed of the second rubber-elastic material and extends from the proximal end of the fingerstall to the walls of the enclosed hollow chamber.

4. The fingerstall according to claim 3, wherein the region is in the form of stripes or ribs.

5. The fingerstall according to claim 1, wherein the outer sheath further comprises a reinforced region extending from the proximal end of the fingerstall to a set of walls of the enclosed hollow chamber.

6. The fingerstall according to claim 5, wherein said reinforced region is one of continuously formed with the outer sheath and fixedly joined to the outer sheath.

7. A kit comprising fingerstalls according to claim 1, wherein the kit comprises fingerstalls of different diameters.

8. The kit according to claim 7, wherein the kit further comprises at least one measuring instrument for determining finger diameters.

9. The fingerstall according to claim 1, wherein the fingerstall comprises a rubber elastic material.

10. The fingerstall according to claim 1, wherein the fluid channel comprises a capillary extending axially in the fingerstall into the enclosed hollow chamber.

11. The fingerstall according to claim 1, wherein the enclosed hollow chamber is substantially spherical or elliptical.

12. The fingerstall according to claim 1, wherein the fingerstall consists of a silicone-based rubber-elastic material.

13. A method for using a fingerstall according to claim 1, for treating a defect on the distal phalanx of the finger, comprising:

selecting a fingerstall having the diameter of a measured finger: and covering the measured finger with the fingerstall.

* * * * *